United States Patent
Shirai et al.

(10) Patent No.: US 11,179,345 B2
(45) Date of Patent: Nov. 23, 2021

(54) WATER-BASED ADHESIVE PATCH

(71) Applicant: TEIKOKU SEIYAKU CO., LTD., Kagawa (JP)

(72) Inventors: Sadanobu Shirai, Takamatsu (JP); Masahiro Inazuki, Naruto (JP)

(73) Assignee: TEIKOKU SEIYAKU CO., LTD., Kagawa (JP)

(*) Notice: Subject to any disclaimer, the term of this patent is extended or adjusted under 35 U.S.C. 154(b) by 0 days.

(21) Appl. No.: 16/341,081

(22) PCT Filed: Oct. 11, 2017

(86) PCT No.: PCT/JP2017/036780
§ 371 (c)(1),
(2) Date: Apr. 11, 2019

(87) PCT Pub. No.: WO2018/070406
PCT Pub. Date: Apr. 19, 2018

(65) Prior Publication Data
US 2019/0231708 A1    Aug. 1, 2019

(30) Foreign Application Priority Data

Oct. 12, 2016 (JP) .............. JP2016-201134

(51) Int. Cl.
*A61K 9/70* (2006.01)
*A61K 31/192* (2006.01)
(Continued)

(52) U.S. Cl.
CPC .............. *A61K 9/7038* (2013.01); *A61K 9/70* (2013.01); *A61K 9/7023* (2013.01);
(Continued)

(58) Field of Classification Search
None
See application file for complete search history.

(56) References Cited

U.S. PATENT DOCUMENTS 4,927,854 A    5/1990  Sunshine et al.
5,776,484 A    7/1998  Sasaki et al.
(Continued)

FOREIGN PATENT DOCUMENTS

EP    2 228 063    9/2010
EP    3 205 341    8/2017
(Continued)

OTHER PUBLICATIONS

International Search Report dated Nov. 21, 2017 /in International Application No. PCT/JP2017/036780, with English translation.
(Continued)

*Primary Examiner* — Bethany P Barham
*Assistant Examiner* — Barbara S Frazier
(74) *Attorney, Agent, or Firm* — Wenderoth, Lind & Ponack, L.L.P.

(57) ABSTRACT

The present invention provides an aqueous patch which can stably contain only one of an S-enantiomer and an R-enantiomer of a drug capable of being present in such enantiomers at a relatively high concentration over a long period of time, has the excellent adhesive property and the excellent shape retaining property, and achieves high skin permeability of the drug. Specifically, the present invention provides an aqueous patch containing only one of enantiomers of a drug as an active ingredient in a pasty preparation.

7 Claims, 1 Drawing Sheet

(51) Int. Cl.
*A61K 47/18* (2017.01)
*A61P 29/00* (2006.01)

(52) U.S. Cl.
CPC .......... *A61K 9/7092* (2013.01); *A61K 31/192* (2013.01); *A61K 47/18* (2013.01); *A61P 29/00* (2018.01)

(56) References Cited

U.S. PATENT DOCUMENTS

| | | | | |
|---|---|---|---|---|
| 5,807,568 | A * | 9/1998 | Cody | A61K 9/0014 424/444 |
| 5,879,702 | A | 3/1999 | Sasaki et al. | |
| 2009/0022778 | A1 | 1/2009 | Yamaji et al. | |
| 2011/0319399 | A1 | 12/2011 | Miura et al. | |
| 2016/0136277 | A1 | 5/2016 | Tani | |

FOREIGN PATENT DOCUMENTS

| | | |
|---|---|---|
| JP | 6-502174 | 3/1994 |
| JP | 6-199701 | 7/1994 |
| JP | 8-119859 | 5/1996 |
| JP | 2001-97852 | 4/2001 |
| JP | 2001-302501 | 10/2001 |
| WO | 92/05769 | 4/1992 |
| WO | 01/02015 | 1/2001 |
| WO | 2006/092829 | 9/2006 |
| WO | 2010/103844 | 9/2010 |
| WO | 2012/151427 | 11/2012 |
| WO | 2016/056356 | 4/2016 |

OTHER PUBLICATIONS

International Preliminary Report on Patentability dated Apr. 25, 2019 in International Application No. PCT/JP2017/036780.
Sugimoto, Masanori et al., "Analgesic Effect of the Newly Developed S(+)-Flurbiprofen Plaster on Inflammatory Pain in a Rat Adjuvant-Induced Arthritis Model", Drug Development Research, Jan. 13, 2016, vol. 77, No. 1, pp. 20-28, ISSN:1098-2299.
Extended European Search Report dated Mar. 17, 2020 in corresponding European Patent Application No. 17860262.9.

* cited by examiner

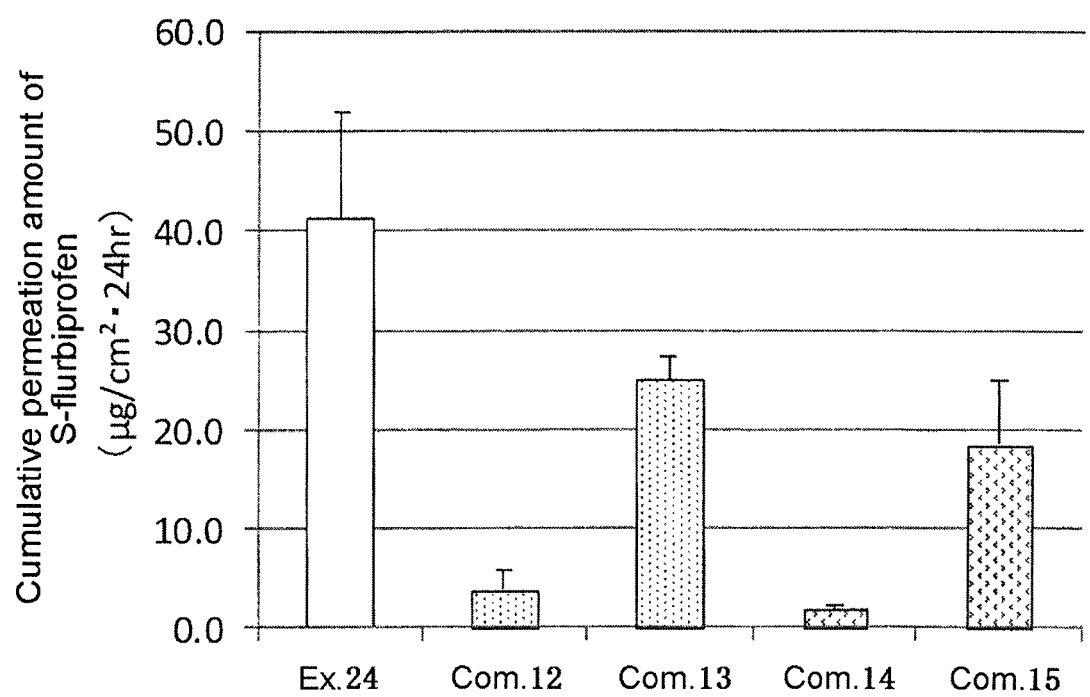

WATER-BASED ADHESIVE PATCH

TECHNICAL FIELD

The present invention relates to an aqueous patch which stably comprises an optically active drug at a relatively high concentration over a long period of time and has excellent skin permeability of the drug in order to enhance the therapeutic effect of the aqueous patch comprising the optically active drug.

BACKGROUND ART

Some drugs have an S-enantiomer and an R-enantiomer. For example, flurbiprofen, which is an anti-inflammatory analgesic, has (+)-2-(2-fluoro-4-biphenyl)propionic acid (hereinafter referred to as S-flurbiprofen) and (−)-2-(2-fluoro-4-biphenyl)propionic acid (hereinafter referred to as R-flurbiprofen) as enantiomers.

Regarding flurbiprofen, an inexpensive racemate comprising an equal amount of the enantiomers, i.e. S-flurbiprofen and R-flurbiprofen (hereinafter referred to as racemic flurbiprofen) is usually used in the pharmaceutical field.

Recently, Patent Document 1 and Patent Document 2 disclose techniques which relate to an aqueous patch (or cataplasm or poultice) comprising an S-enantiomer of an anti-inflammatory analgesic. Patent Document 1 discloses an external formulation comprising S-flurbiprofen and a polyhydric alcohol, and also discloses an aqueous patch as an example thereof. Also, Patent Document 2 discloses an aqueous patch comprising S-flurbiprofen which comprises sodium carboxymethyl cellulose and sodium polyacrylate as base ingredients.

These Patent Documents suggest the possibility of the improvement of therapeutic effect of the aqueous patches by using an S-enantiomer having a potent pharmacological effect. However, the formulation stability of such patches has hardly been studied so far. Especially, such patches have many respects to be improved such as the drug solubility in a formulation comprising a relatively high concentration of the drug, or the maintenance of the drug solubility and formulation property of a formulation stored over a long period of time. Thus, it has been desired to provide an aqueous patch having both improved therapeutic effects and formulation stability.

CITATION LIST

Patent Document

Patent Document 1: JPH 06-199701 A
Patent Document 2: JPH 08-119859 A

SUMMARY OF INVENTION

Technical Problem

Generally, a higher drug concentration is expected to result in better transdermal absorbability and a therapeutic effect. Accordingly, an enhanced therapeutic effect may be achieved by increasing the amount of drug. However, many drugs which have been used in transdermal formulations are highly lipophilic, and it is very difficult to stably incorporate such drugs into an aqueous patch comprising water as a main ingredient at a high concentration and a dissolved state.

For example, it is difficult to incorporate S-flurbiprofen into a pasty preparation at a high concentration in a conventional aqueous patch, and the concentration thereof is very low and about 0.3 w/w % at the highest relative to the pasty preparation weight.

In the case of flurbiprofen, although the S-enantiomer drug, i.e. S-flurbiprofen per se has a very potent anti-inflammatory action, a further therapeutic effect cannot be expected without incorporating it into an aqueous patch at a high concentration to some extent. Accordingly, it is a major problem for the practical application to stably maintain a high concentration of drug in a formulation over a long period of time.

Solution to Problem

The present inventors have earnestly studied to solve the above problems, and as a result found that an aqueous patch, which has excellent adhesive property and shape retaining property, can stably comprise a drug at a relatively high concentration over a long period of time, and shows further high skin permeability of the drug, may be prepared by using only one of the enantiomers of the drug having an S-enantiomer and an R-enantiomer as enantiomers preferably in combination with a water-soluble organic amine, further preferably by mixing the drug with a pasty preparation base comprising an appropriate combination of water, a humectant, a water-soluble polymer, a cross-linking agent, a pH regulator, and the like, and finally completed the present invention.

Namely, the present invention relates to the followings.
[1] An aqueous patch comprising only one of enantiomers of a drug as an active ingredient in a pasty preparation.
[2] The aqueous patch according to [1], wherein the drug is an antiphlogistic or an analgesic, or an auxiliary agent thereof.
[3] The aqueous patch according to [1] or [2], wherein the drug is one or more selected from flurbiprofen, ketoprofen, and ibuprofen.
[4] The aqueous patch according to any one of [1] to [3], wherein the drug is flurbiprofen.
[5] The aqueous patch according to any one of [1] to [4], wherein the amount of the drug is 0.5 to 6 w/w % relative to the pasty preparation weight.
[6] The aqueous patch according to any one of [1] to [5], which further comprises a water-soluble organic amine in the pasty preparation.
[7] The aqueous patch according to [6], wherein the water-soluble organic amine is one or more selected from monomethanolamine, monoethanolamine, monopropanolamine, monoisopropanolamine, dimethanolamine, diethanolamine, dipropanolamine, diisopropanolamine, dibutanolamine, diisobutanolamine, trimethanolamine, triethanolamine, tripropanolamine, triisopropanolamine, tributanolamine, triisobutanolamine, methylamine, ethylamine, propylamine, dimethylamine, diethylamine, dipropylamine, diisopropylamine, trimethylamine, triethylamine, tripropylamine, and triisopropylamine.
[8] The aqueous patch according to [6] or [7], wherein the amount of the water-soluble organic amine is 0.2 to 5 w/w % relative to the pasty preparation weight.
[9] The aqueous patch according to any one of [6] to [8], wherein the weight ratio of the water-soluble organic amine relative to the enantiomer of the drug is 0.25 to 5.
[10] The aqueous patch according to any one of [1] to [9], wherein the enantiomer of the drug is an S-enantiomer.
[11] The aqueous patch according to any one of [1] to [10], which further comprises one or more ingredient(s) selected from water, polyacrylic acid or a salt thereof, a cellulose derivative, a cross-linking agent, a humectant, and a pH regulator in the pasty preparation.

[12] The aqueous patch according to [11], wherein the polyacrylic acid or a salt thereof is one or more selected from polyacrylic acid, sodium polyacrylate, and partially neutralized polyacrylate;

the cellulose derivative is one or more selected from sodium carboxymethyl cellulose, hydroxypropyl cellulose, and hydroxymethyl cellulose;

the cross-linking agent is one or more selected from dihydroxyaluminum aminoacetate, magnesium aluminometasilicate, aluminum hydroxide, and synthetic hydrotalcite;

the humectant is one or more selected from glycerin, 1,3-butylene glycol, propylene glycol, polypropylene glycol, D-sorbitol, and polyethylene glycol 400; and the pH regulator is one or more selected from tartaric acid, lactic acid, and malic acid.

[13] The aqueous patch according to [11] or [12], wherein the amount of the water is 20 to 70 w/w %, the amount of the polyacrylic acid or a salt thereof is 2 to 20 w/w %, the amount of the cellulose derivative is 2 to 20 w/w %, the amount of the cross-linking agent is 0.02 to 3.5 w/w %, the amount of the humectant is 5 to 60 w/w %, and the amount of the pH regulator is 0.2 to 10 w/w %, relative to the pasty preparation weight.

Further, the present invention also relates to the followings.

[14] The aqueous patch according to any one of [1] to [13], wherein the drug is one or more selected from S-flurbiprofen, S-ketoprofen, and S-ibuprofen.

[15] The aqueous patch according to any one of [1] to [14], wherein the drug is S-flurbiprofen.

[16] The aqueous patch according to any one of [6] to [15], wherein the water-soluble organic amine is one or more selected from diisopropanolamine, monoethanolamine, diethanolamine, triethanolamine, and triethylamine.

[17] The aqueous patch according to any one of [1] to [16], which further comprises crotamiton in the pasty preparation.

[18] The aqueous patch according to any one of [1] to [17], which further comprises one or more ingredient(s) selected from a water-soluble polymer other than the polyacrylic acid or a salt thereof and the cellulose derivative, an excipient, a stabilizing agent, and a preservative in the pasty preparation.

[19] The aqueous patch according to any one of [1] to [18], wherein the pasty preparation consists of one of the enantiomers of the drug, a water-soluble organic amine, water, a polyacrylic acid or a salt thereof, a cellulose derivative, a cross-linking agent, a humectant, and a pH regulator, and one or more ingredient(s) selected from crotamiton, a water-soluble polymer other than the polyacrylic acid or a salt thereof and the cellulose derivative, an excipient, a stabilizing agent, and a preservative as optional ingredient(s).

Effect of Invention

According to the present invention, an aqueous patch, which can stably comprise and maintain a drug in a formulation at a high concentration, shows high skin permeability of the drug, and has excellent adhesive property and shape retaining property, can be provided by using only one of enantiomers of the drug in aqueous patch, preferably by combining the enantiomer with a water-soluble organic amine.

BRIEF DESCRIPTION OF DRAWINGS

FIG. 1 A FIGURE showing cumulative skin permeation amounts of S-flurbiprofen using an aqueous patch of the present invention and aqueous patches of Comparative Examples.

DESCRIPTION OF EMBODIMENTS

Hereinafter, aqueous patches of the present invention are illustrated further in detail.

Aqueous patches of the present invention are aqueous patches which usually stably comprise a drug in a pasty preparation at a relatively high concentration in order to achieve high therapeutic effects, which achieve excellent skin permeation amounts of the drug, and which achieve excellent storage stability of the drug. The pasty preparation is an adhesive pasty composition comprising a drug. Also, a pasty preparation base means a mixture of ingredient(s) constituting the pasty preparation except for a drug.

The drug which may be contained in the aqueous patch of the present invention is not limited as long as it has an S-enantiomer and an R-enantiomer as enantiomers. Examples of the drug include an antiphlogistic or an analgesic, or an auxiliary agent thereof; an antihypertensive; an antiemetic; a cerebral circulation improving agent; an antidepressant; a sex hormone; an antitussive; an anti-tumor agent; an antihistamine; a coronary vasodilator; an antifungal agent; an antibacterial agent; a general anesthetic; a sedative hypnotic; an antidementia drug; an antiparkinson drug; a tranquilizer; a disinfectant, and the like, and an antiphlogistic or an analgesic, or an auxiliary agent thereof, which is expected to achieve a combined action with cool feeling caused by the aqueous patch, is preferable. Examples of the antiphlogistic or the analgesic, or an auxiliary agent thereof which may be used in the aqueous patch of the present invention include an anti-inflammatory analgesic, a local anesthetic, an opioid, an opioid antagonist, and the like, and specific examples thereof include flurbiprofen, ketoprofen, ibuprofen, naproxen, loxoprofen, zaltoprofen, ketorolac, cortisol, prednisolone, methylprednisolone, triamcinolone, dexamethasone, betamethasone, morphine, oxycodone, methadone, codeine, buprenorphine, tramadol, tapentadol, pentazocine, nalorphine, butorphanol, levallorphan, eptazocine, nalbuphine, nalfurafine, naloxone, prilocaine, mepivacaine, bupivacaine, ropivacaine, and a pharmaceutically acceptable salt or ester thereof. Any one of them or a combination of two or more of them may be used. A preferable antiphlogistic or analgesic, or an auxiliary agent thereof is an anti-inflammatory analgesic, further preferably is one or more selected from flurbiprofen, ketoprofen, and ibuprofen, and especially preferably is flurbiprofen. Although each of these drugs has an S-enantiomer and an R-enantiomer as enantiomers, the enantiomer to be used must be the only one of them, may be an S-enantiomer only or an R-enantiomer only, and preferably an S-enantiomer which has a prominent pharmacological effect. However, the amount of the other enantiomer unavoidably incorporated in the preparation of an active pharmaceutical ingredient, or the amount of the other enantiomer produced by decomposition reaction in the storage of an active pharmaceutical ingredient is very small and causes substantially no problem.

The amount of the drug is preferably 0.5 to 6 w/w %, more preferably 1 to 3 w/w %, and further preferably 1 to 2 w/w %, relative to the pasty preparation weight. When the amount is less than 0.5 w/w %, the therapeutic effect decreases. When the amount is more than 6 w/w %, the drug may precipitate in the pasty preparation and the transdermal absorbability from the aqueous patch may decrease. When the term "relatively high concentration" is used in relation to the amount of the drug in the present description, said term refers to the above range.

In one embodiment, the aqueous patch of the present invention comprises a water-soluble organic amine in the pasty preparation. The water-soluble organic amine has a function of stably dissolving one of enantiomers of a drug into the pasty preparation.

In the present description, the water-soluble organic amine is an amine substituted with 1 to 3 unsubstituted alkyl group(s) (for example, $C_1$-$C_4$ alkyl group) or 1 to 3 alkyl group(s) (for example, $C_1$-$C_4$ alkyl group) having substituent(s), preferably 1 to 3 hydroxy group(s), and further selected from those which are stably dissolved into water, and are preferably monomethanolamine, monoethanolamine, monopropanolamine, monoisopropanolamine, dimethanolamine, diethanolamine, dipropanolamine, diisopropanolamine, dibutanolamine, diisobutanolamine, trimethanolamine, triethanolamine, tripropanolamine, triisopropanolamine, tributanolamine, triisobutanolamine, methylamine, ethylamine, propylamine, dimethylamine, diethylamine, dipropylamine, diisopropylamine, trimethylamine, triethylamine, tripropylamine, triisopropylamine, and the like, and any one or a combination of two or more of them may be used. More preferably, the water-soluble organic amine is any one of or a combination of two or more selected from diisopropanolamine, monoethanolamine, diethanolamine, triethanolamine, and triethylamine.

The amount of the water-soluble organic amine is adjusted based on the amount of one enantiomer of a drug, and preferably 0.2 to 5 w/w %, more preferably 0.5 to 3 w/w %, further preferably 0.8 to 2 w/w %, relative to the pasty preparation weight. The amount of less than 0.2 w/w % is not preferable, because the drug cannot be dissolved into the pasty preparation. The amount of more than 5 w/w % is not preferable, because the adhesive force of the pasty preparation decreases.

The ratio (weight ratio) of the water-soluble organic amine relative to the enantiomer of the drug is preferably 0.25 to 5, more preferably 0.25 to 3, and further preferably 0.3 to 1. The amount of less than 0.25 is not preferable, because the drug precipitates in the pasty preparation. The amount of more than 5 is not preferable, because the adhesive property and the shape retaining property of the pasty preparation decrease.

In one embodiment, the aqueous patch of the present invention may comprise one or more ingredient(s) selected from water, a water-soluble polymer, a cross-linking agent, a humectant, and a pH regulator in the pasty preparation.

Water is a medium for dissolving the water-soluble polymer, and the amount thereof is preferably 20 to 70 w/w %, more preferably 30 to 60 w/w %, and further preferably 30 to 50 w/w %, relative to the pasty preparation weight. When the amount is less than 20 w/w %, the water-soluble polymer is not sufficiently dissolved therein, the resulting mixture becomes unhomogeneous, and the adhesive force and the shape retaining property of the pasty preparation becomes poor. The amount of more than 70 w/w % is not preferable, because the shape retaining property of the pasty preparation weakens. In the description, said amount of water means the total amount of water which comprises purified water added in the preparation of the patch and water contained in other ingredient(s) (for example, sorbitol solution).

The water-soluble polymer is dissolved into water to have a thickening function and form a crosslinked polymer, and has functions to enhance the adhesive force of the pasty preparation and maintain the shape retaining property. Usually, polyacrylic acid or a salt thereof and a material selected from cellulose derivatives are used in combination as the water-soluble polymer.

Polyacrylic acid or a salt thereof is dissolved into water to have a thickening function and forms a crosslinked polymer by a cross-linking agent, to enhance the adhesive force of the pasty preparation. Examples of the polyacrylic acid or a salt thereof include polyacrylic acid, sodium polyacrylate, and partially neutralized polyacrylate. Any one or a combination of two or more of them may be used, and a combination of polyacrylic acid and sodium polyacrylate is preferable.

The amount of polyacrylic acid or a salt thereof is preferably 2 to 20 w/w %, more preferably 3 to 15 w/w %, and further preferably 5 to 10 w/w %, relative to the pasty preparation weight. When the amount is less than 2 w/w %, the adhesive force of the pasty preparation decreases. When the amount is more than 20 w/w %, polyacrylic acid or a salt thereof is partially undissolved into water, the pasty preparation becomes unhomogeneous, and the adhesive force thereof becomes poor.

The cellulose derivative dissolves into water to have a thickening function, thereby has a function to control the shape retaining property of the pasty preparation. Examples of the cellulose derivative include sodium carboxymethyl cellulose, hydroxypropyl cellulose, and hydroxymethyl cellulose. Any one or a combination of two or more of them may be used, and especially one or a combination of two or more comprising sodium carboxymethyl cellulose is preferable.

The amount of the cellulose derivative is preferably 2 to 20 w/w %, more preferably 3 to 15 w/w %, and further preferably 3 to 10 w/w %, relative to the pasty preparation weight. When the amount is less than 2 w/w %, the viscosity decreases and the shape retaining property of the pasty preparation cannot be maintained. When the amount is more than 20 w/w %, the cellulose derivative is partially undissolved into water, the pasty preparation becomes unhomogeneous, and the shape retaining property cannot be maintained constant.

The cross-linking agent has functions to form a crosslinked polymer of polyacrylic acid or a salt thereof and maintain the shape retaining property of the pasty preparation, and selected from poorly-soluble multivalent metal salts. Example thereof include dihydroxyaluminum aminoacetate, magnesium aluminometasilicate, aluminum hydroxide, and synthetic hydrotalcite. Any one or a combination of two or more of them may be used, and one or more selected from dihydroxyaluminum aminoacetate, magnesium aluminometasilicate, and synthetic hydrotalcite is/are preferable.

The amount of the cross-linking agent is preferably 0.02 to 3.5 w/w %, more preferably 0.03 to 2 w/w %, and further preferably 0.04 to 0.5 w/w %, relative to the pasty preparation weight. When the amount is less than 0.02 w/w %, a crosslinked polymer is not sufficiently formed, and the shape retaining property of the pasty preparation is deteriorated. When the amount is more than 3.5 w/w %, a crosslinked polymer is excessively formed, and the adhesive property of the formulation is deteriorated.

The humectant has functions to enhance a moisturizing effect on a skin and control the shape retaining property of the pasty preparation.

The humectant is selected from polyhydric alcohols which can be dissolved into water, preferably glycerin, 1,3-butylene glycol, propylene glycol, polypropylene glycol, D-sorbitol, and polyethylene glycol 400, and any one or a combination of two or more of them may be used. Especially, any one or a combination of two or more selected from glycerin, propylene glycol, and D-sorbitol is preferable.

The amount of the humectant is preferably 5 to 60 w/w %, more preferably 10 to 50 w/w %, and further preferably 20 to 40 w/w %, relative to the pasty preparation weight. The amount of less than 5 w/w % is not preferable, because the shape retaining property of the pasty preparation becomes poor. The amount of more than 60 w/w % is not preferable, because the amount(s) of other material(s), especially the amount of water becomes insufficient, and the adhesive property and the shape retaining property of the pasty preparation become poor.

The pH regulator has functions to regulate the pH of the pasty preparation, and selected from organic acids. Examples thereof include tartaric acid, lactic acid, and malic acid. Any one or a combination of two or more of them may be used, and tartaric acid is preferable.

The amount of the pH regulator is preferably 0.2 to 10 w/w %, more preferably 0.3 to 7 w/w %, and further preferably 0.5 to 5 w/w %, relative to the pasty preparation weight. It is preferable to control the pH of the pasty preparation within a range of 4 to 7 in order to maintain a drug at a dissolved state in the pasty preparation and maintain the adhesive force and the shape retaining property.

Also, the present inventors have studied the material(s) to stabilize the dissolved state of a drug under an environmental condition such as a very long period of cold storage, and found that crotamiton can be used in the aqueous base. The amount thereof is preferably 0.1 to 3 w/w %, more preferably 0.1 to 2 w/w %, and further preferably 0.1 to 1 w/w %, relative to the pasty preparation weight.

Further, the aqueous patch of the present invention may comprise other therapeutically effective drug(s). Also, materials generally used in an aqueous patch, for example a water-soluble polymer other than the above polyacrylic acid or a salt thereof and cellulose derivative (for example polyvinyl alcohol or the like, and the amount thereof is 0.1 to 3 w/w %, more preferably 0.1 to 2 w/w %, and further preferably 0.1 to 1 w/w %, relative to the pasty preparation weight), an excipient (for example kaolin or the like, and the amount thereof is 0.1 to 10 w/w %, more preferably 0.3 to 5 w/w %, and further preferably 0.5 to 3 w/w %, relative to the pasty preparation weight), a stabilizing agent (for example sodium edetate or the like, and the amount thereof is 0.01 to 1 w/w %, more preferably 0.03 to 0.5 w/w %, and further preferably 0.05 to 0.1 w/w %, relative to the pasty preparation weight), a preservative (for example p-hydroxybenzoate ester or the like, and the amount thereof is 0.1 to 3 w/w %, more preferably 0.1 to 2 w/w %, and further preferably 0.1 to 1 w/w %, relative to the pasty preparation weight), and the like may be used, as long as they do not deteriorate the transdermal absorbability and decrease the therapeutic effect due to the precipitation of the drug etc. in the pasty preparation caused by the volatilization of the materials per se under a long period of storage or in use.

In the aqueous patch of the present invention, the pasty preparation is spread or applied between a backing and a release liner. The backing is not specifically limited, as long as it can retain the applied pasty preparation. Examples of the backing include a fabric such as a non-woven fabric and a woven fabric, a material prepared by binding a thin plastic film to a fabric, and a laminate material having a thin film between fabrics. Examples of the material of these backings include polyethylene, polypropylene, polyvinyl chloride, polyester, polyethylene terephthalate, nylon, polyurethane, rayon, polyacrylonitrile, polystyrene, and polyethylene naphthalate. The backing may be or may not be air permeable. In the case of a laminate material, a film per se may be moisture permeability, or a film may be subjected to an appropriate treatment such as making through-holes.

The application method of the pasty preparation to the backing is not specifically limited, and a common method for producing an aqueous patch is used. The weight of the applied pasty preparation is preferably 200 to 1500 $g/m^2$, and more preferably 300 to 1200 $g/m^2$. A finished product of the aqueous patch may be cut into an appropriate shape and size depending on the diseased area.

Examples of the material of the release liner include polyester, polyethylene terephthalate, polypropylene, and paper, and polyester is especially preferable. The release liner may be siliconized if necessary to optimize the peel force.

Hereinafter, the present invention is specifically illustrated by means of Examples (Ex.), Comparative Examples (Com.), and Test Examples, but is not limited to these Examples.

EXAMPLES

Example 1

An aqueous patch was prepared by using the ingredients described in Table 1 and the following procedures.

S-Flurbiprofen and diisopropanolamine were added to purified water and dissolved therein (Solution).

Sodium polyacrylate, partially neutralized polyacrylate, sodium carboxymethyl cellulose, hydroxypropyl cellulose, and synthetic hydrotalcite were added to concentrated glycerin and dispersed therein (Dispersion).

Purified water, a solution obtained by dissolving polyvinyl alcohol in purified water, a solution obtained by dissolving polyacrylic acid in purified water, a sorbitol solution (70% D-sorbitol), kaolin, and tartaric acid were mixed, and the resulting liquid was stirred and gradually mixed with the Dispersion. Then, the Solution was added thereto, and the resulting mixture was stirred to prepare a pasty preparation.

The pasty preparation was spread between a non-woven fabric and a polyester film and cut into an appropriate size to prepare an aqueous patch.

Example 2

A desired aqueous patch was prepared by using the ingredients described in Table 1 according to the procedures described in Example 1.

Comparative Examples 1, 2, and 3

Desired aqueous patches were prepared by using the ingredients described in Table 1 according to the procedures described in Example 1.

TABLE 1

| Ingredients | Ex. 1 | Ex. 2 | Com. 1 | Com. 2 | Com. 3 |
|---|---|---|---|---|---|
| S-Flurbiprofen | 2 | | 1 | 1.6 | 1.8 |
| R-Flurbiprofen | | 2 | 1 | 0.4 | 0.2 |
| Diisopropanolamine | 1 | 1 | 1 | 1 | 1 |
| Concentrated glycerin | 20 | 20 | 20 | 20 | 20 |
| Sodium polyacrylate | 3 | 3 | 3 | 3 | 3 |
| Partially neutralized polyacrylate | 2 | 2 | 2 | 2 | 2 |
| Sodium carboxymethyl cellulose | 3.5 | 3.5 | 3.5 | 3.5 | 3.5 |
| Hydroxypropyl cellulose | 0.5 | 0.5 | 0.5 | 0.5 | 0.5 |
| Synthetic hydrotalcite | 0.07 | 0.07 | 0.07 | 0.07 | 0.07 |
| Polyvinyl alcohol | 0.5 | 0.5 | 0.5 | 0.5 | 0.5 |
| Polyacrylic acid | 2 | 2 | 2 | 2 | 2 |
| Sorbitol solution | 20 | 20 | 20 | 20 | 20 |
| Kaolin | 2 | 2 | 2 | 2 | 2 |
| Tartaric acid | 0.5 | 0.5 | 0.5 | 0.5 | 0.5 |
| Purified water | 42.93 | 42.93 | 42.93 | 42.93 | 42.93 |
| Pasty preparation weight | 400 g/m$^2$ | 400 g/m$^2$ | 400 g/m$^2$ | 400 g/m$^2$ | 400 g/m$^2$ |
| (Diisopropanolamine)/ (S-Flurbiprofen and/or R-Flurbiprofen) (weight ratio) | 0.50 | 0.50 | 0.50 | 0.50 | 0.50 | amount (w/w %)

Test Example 1

The presence or absence of crystal precipitation of the drug in the pasty preparation of each formulation prepared above was observed by using a polarizing microscope.

The results are shown in Table 2.

As shown in Table 2, while precipitation of the drug in the pasty preparation was not observed in the patches of Example 1 and Example 2, crystal precipitation of the drug was observed in all the patches of Comparative Examples. Especially, the patch of Comparative Example 1 comprising enantiomers in the ratio of 1:1 (racemate) showed large amount of crystal precipitation of the drug. While the formulations comprising only one of the enantiomers of the drug could dissolve the drug well, the formulations comprising a mixture of enantiomers showed significantly poorer solubility.

TABLE 2

| Pasty preparation | Example 1 | Example 2 | Comparative Example 1 | Comparative Example 2 | Comparative Example 3 |
|---|---|---|---|---|---|
| Crystal precipitation of the drug | No precipitate | No precipitate | Large amount of precipitate | Certain degree of precipitate | Certain degree of precipitate |

Examples 3, 4, 5, and 6

Desired aqueous patches were prepared by using the ingredients described in Table 3 according to the procedures described in Example 1.

Comparative Examples 4 and 5

Desired aqueous patches were prepared by using the ingredients described in Table 3 according to the procedures described in Example 1.

TABLE 3

| Ingredients | Ex. 3 | Ex. 4 | Ex. 5 | Ex. 6 | Com. 4 | Com. 5 |
|---|---|---|---|---|---|---|
| S-Flurbiprofen | 1.5 | 1.5 | 1.5 | 1.5 | 1.5 | 1.5 |
| Diisopropanolamine | 1 | | 0.5 | | | |
| Triethanolamine | | 1 | 0.5 | | | |
| Triethylamine | | | | 1 | | |
| Sodium hydroxide | | | | | | 1 |
| Concentrated glycerin | 20 | 20 | 20 | 20 | 20 | 20 |
| Partially neutralized polyacrylate | 4 | 4 | 4 | 4 | 4 | 4 |
| Sodium carboxymethyl cellulose | 4 | 4 | 4 | 4 | 4 | 4 |
| Synthetic hydrotalcite | 0.08 | 0.08 | 0.08 | 0.08 | 0.08 | 0.08 |
| Polyacrylic acid | 4 | 4 | 4 | 4 | 4 | 4 |
| Sorbitol solution | 15 | 15 | 15 | 15 | 15 | 15 |
| Kaolin | 2 | 2 | 2 | 2 | 2 | 2 |
| Tartaric acid | 1 | 1 | 1 | 1 | 1 | 1 |

TABLE 3-continued

| Ingredients | Ex. 3 | Ex. 4 | Ex. 5 | Ex. 6 | Com. 4 | Com. 5 |
|---|---|---|---|---|---|---|
| Purified water | 47.42 | 47.42 | 47.42 | 47.42 | 48.42 | 47.42 |
| Pasty preparation weight | 800 g/m² | 800 g/m² | 800 g/m² | 800 g/m² | 800 g/m² | 800 g/m² |
| Water-soluble organic amine/ S-Flurbiprofen (weight ratio) | 0.67 | 0.67 | 0.67 | 0.67 | — | — | amount (w/w %)

Test Example 2

The presence or absence of crystal precipitation of the drug in the pasty preparation of each formulation prepared above was observed by using a polarizing microscope. Also, a rubber roll was rolled over the pasty preparation of each formulation, and the adhesive property and the shape retaining property of the pasty preparation were observed.

The results are shown in Table 4.

As shown in Table 4, precipitation of the drug in the pasty preparation was not observed in the patches of Examples 3 to 6. On the other hand, in the patch of Comparative Example 4, drug precipitation was observed, and the adhesive force of the pasty preparation was deteriorated. In the patch of Comparative Example 5, crystal precipitation of the drug was observed, the adhesive property and the shape retaining property of the pasty preparation were poor, and the formulation could not be used as an aqueous patch.

It is believed that the patch of Comparative Example 4 was free of a water-soluble organic amine and thus S-flurbiprofen was not dissolved in the pasty preparation, and the patch of Comparative Example 5 used an inorganic water-soluble alkali metal salt, sodium hydroxide, instead of a water-soluble organic amine, and thus S-flurbiprofen was not stably dissolved in the pasty preparation.

TABLE 4

| Pasty preparation | Ex. 3 | Ex. 4 | Ex. 5 | Ex. 6 | Com. 4 | Com. 5 |
|---|---|---|---|---|---|---|
| Crystal precipitation of the drug | No precipitate | No precipitate | No precipitate | No precipitate | Large amount of precipitate | Large amount of precipitate |
| Adhesive property and shape retaining property | Excellent | Excellent | Excellent | Excellent | Deteriorated adhesive property | Poor adhesive property and shape retaining property |

Examples 7 and 8

Desired aqueous patches were prepared by using the ingredients described in Table 5 according to the procedures described in Example 1.

Comparative Examples 6 and 7

Desired aqueous patches were prepared by using the ingredients described in Table 5 according to the procedures described in Example 1.

TABLE 5

| Ingredients | Ex. 7 | Ex. 8 | Com. 6 | Com. 7 |
|---|---|---|---|---|
| S-Flurbiprofen | 2 | 2 | 2 | 2 |
| Diisopropanolamine | 1 | 3 | 0.1 | 6 |

TABLE 5-continued

| Ingredients | Ex. 7 | Ex. 8 | Com. 6 | Com. 7 |
|---|---|---|---|---|
| Concentrated glycerin | 20 | 20 | 20 | 20 |
| Sodium polyacrylate | 5 | 5 | 5 | 5 |
| Sodium carboxymethyl cellulose | 4 | 4 | 4 | 4 |
| Dihydroxyaluminum aminoacetate | 0.07 | 0.07 | 0.07 | 0.07 |
| Polyacrylic acid | 2 | 2 | 2 | 2 |
| Sorbitol solution | 20 | 20 | 20 | 20 |
| Kaolin | 1 | 1 | 1 | 1 |
| Tartaric acid | 1 | 1 | 1 | 1 |
| Sodium edetate | 0.07 | 0.07 | 0.07 | 0.07 |
| Purified water | 43.86 | 41.86 | 44.76 | 38.86 |
| Pasty preparation weight | 1200 g/m² | 1200 g/m² | 1200 g/m² | 1200 g/m² |
| Diisopropanolamine/ S-Flurbiprofen (weight ratio) | 0.50 | 1.50 | 0.05 | 3.00 | amount (w/w %)

Test Example 3

The presence or absence of crystal precipitation of the drug in the pasty preparation of each formulation prepared above was observed by using a polarizing microscope. Also, a rubber roll was rolled over the pasty preparation of each formulation, and the adhesive property and the shape retaining property of the pasty preparation were observed.

The results are shown in Table 6.

As shown in Table 6, regarding the patches of Examples 7 and 8, crystal precipitation of the drug was not observed in the pasty preparation, and the adhesive property and the shape retaining property of the pasty preparation were also excellent. In the patch of Comparative Example 6, a large amount of drug precipitation was observed in the pasty preparation. In the patch of Comparative Example 7, drug precipitation was not observed in the pasty preparation, but the pasty preparation was not solidified, the adhesive property and the shape retaining property were poor, and the formulation could not be used as an aqueous patch.

TABLE 6

| Pasty preparation | Ex. 7 | Ex. 8 | Com. 6 | Com. 7 |
|---|---|---|---|---|
| Crystal precipitation of the drug | No precipitate | No precipitate | Large amount of precipitate | No precipitate |
| Adhesive property and shape retaining property | Excellent | Excellent | Excellent | Unsolidified pasty preparation, and significantly poor adhesive property and shape retaining property |

Examples 9, 10, 11, 12, and 13

Desired aqueous patches were prepared by using the ingredients described in Table 7 according to the procedures described in Example 1.

Comparative Examples 8 and 9

Desired aqueous patches were prepared by using the ingredients described in Table 7 according to the procedures described in Example 1.

TABLE 7

| Ingredients | Ex. 9 | Ex. 10 | Ex. 11 | Ex. 12 | Ex. 13 | Com. 8 | Com. 9 |
|---|---|---|---|---|---|---|---|
| S-Flurbiprofen | 1 | 3 | 5 | 6 | 1 | 5 | 1 |
| Diisopropanolamine | 1 | 1 | 5 | 1.5 | 5 | 1 | 6 |
| Concentrated glycerin | 20 | 20 | 20 | 20 | 20 | 20 | 20 |
| Sorbitol solution | 17.5 | 17.5 | 17.5 | 17.5 | 17.5 | 17.5 | 17.5 |
| Polyacrylic acid | 4 | 4 | 4 | 4 | 4 | 4 | 4 |
| Sodium polyacrylate | 5 | 5 | 5 | 5 | 5 | 5 | 5 |
| Sodium carboxymethyl cellulose | 4 | 4 | 4 | 4 | 4 | 4 | 4 |
| Hydroxypropyl cellulose | 0.3 | 0.3 | 0.3 | 0.3 | 0.3 | 0.3 | 0.3 |
| Dihydroxyaluminum aminoacetate | 0.07 | 0.07 | 0.07 | 0.07 | 0.07 | 0.07 | 0.07 |
| Kaolin | 1 | 1 | 1 | 1 | 1 | 1 | 1 |
| Tartaric acid | 1 | 1 | 1 | 1 | 1 | 1 | 1 |
| Sodium edetate | 0.06 | 0.06 | 0.06 | 0.06 | 0.06 | 0.06 | 0.06 |
| Purified water | 45.07 | 43.07 | 37.07 | 39.57 | 41.07 | 41.07 | 40.07 |
| Pasty preparation weight | 1000 g/m$^2$ | 1000 g/m$^2$ | 1000 g/m$^2$ | 1000 g/m$^2$ | 1000 g/m$^2$ | 1000 g/m$^2$ | 1000 g/m$^2$ |
| Diisopropanolamine/S-Flurbiprofen (weight ratio) | 1.00 | 0.33 | 1.00 | 0.25 | 5.00 | 0.20 | 6.00 | amount (w/w %)

Test Example 4

The presence or absence of crystal precipitation of the drug in the pasty preparation of each formulation prepared above was observed by using a polarizing microscope. Also, a rubber roll was rolled over the pasty preparation of each formulation, and the adhesive property and the shape retaining property of the pasty preparation were observed.

The results are shown in Table 8.

As shown in Table 8, regarding the patches of Examples 9 to 13, precipitation of the drug in the pasty preparation was not observed, and the adhesive property and the shape retaining property of the pasty preparation were also Excellent. In the patch of Comparative Example 8, crystal precipitation of the drug was observed in the pasty preparation. In the patch of Comparative Example 9, crystal precipitation of the drug was not observed in the pasty preparation, but the pasty preparation was poorly solidified, the adhesive property and the shape retaining property were poor, and the formulation could not be used as an aqueous patch.

In the patches of Examples 9 to 13, the weight ratio of diisopropanolamine/S-flurbiprofen was within a range of 0.25 to 5. In the patch of Comparative Example 8, said weight ratio was 0.20, which was below 0.25, and the amount of diisopropanolamine is smaller relative to the amount of the drug. As a result, it is believed that the drug precipitated in the pasty preparation. In the patch of Comparative Example 9, the amount of diisopropanolamine is 6 w/w %, and the weight ratio of diisopropanolamine/S-flurbiprofen is 6. It is believed that the amount of diisopropanolamine was too higher in said ratio, and thus the adhesive property and the shape retaining property of the pasty preparation could not be maintained.

TABLE 8

| Pasty preparation | Ex. 9 | Ex. 10 | Ex. 11 | Ex. 12 | Ex. 13 | Com. 8 | Com. 9 |
|---|---|---|---|---|---|---|---|
| Crystal precipitation of the drug | No precipitate | No precipitate | No precipitate | No precipitate | No precipitate | Certain degree of precipitate | No precipitate |
| Adhesive property and shape retaining property | Excellent | Excellent | Excellent | Excellent | Excellent | Excellent | Poorly solidified pasty preparation, and significantly poor adhesive property and shape retaining property |

Examples 14, 15, 16, and 17

Desired aqueous patches were prepared by using the ingredients described in Table 9 according to the procedures described in Example 1.

Comparative Examples 10 and 11

Desired aqueous patches were prepared by using the ingredients described in Table 9 according to the procedures described in Example 1.

TABLE 9

| Ingredients | Ex. 14 | Ex. 15 | Ex. 16 | Ex. 17 | Com. 10 | Com. 11 |
|---|---|---|---|---|---|---|
| S-Flurbiprofen | 1.5 | 1.5 | 1.5 | 1.5 | 1.5 | 1.5 |
| Diisopropanolamine | 1 | 1 | 1 | 3 | 1 | 10 |
| Concentrated glycerin | 20 | 20 | 20 | 20 | 20 | 20 |
| Sorbitol solution | 17.5 | 17.5 | 17.5 | 17.5 | 17.5 | 17.5 |
| Polyacrylic acid | 4 | 4 | 4 | 4 | 4 | 4 |
| Sodium polyacrylate | 5 | 5 | 5 | 5 | 5 | 5 |
| Sodium carboxymethyl cellulose | 4 | 4 | 4 | 4 | 4 | 4 |
| Dihydroxyaluminum aminoacetate | 0.07 | 0.07 | 0.07 | 0.07 | 0.07 | 0.07 |
| Kaolin | 1 | 1 | 1 | 1 | 1 | 1 |
| Tartaric acid | 4 | 3 | 1 | 0.5 | 5 | 0.5 |
| Sodium edetate | 0.06 | 0.06 | 0.06 | 0.06 | 0.06 | 0.06 |
| Purified water | 41.87 | 42.87 | 44.87 | 43.37 | 40.87 | 36.37 |
| Pasty preparation weight | 800 g/m$^2$ | 800 g/m$^2$ | 800 g/m$^2$ | 800 g/m$^2$ | 800 g/m$^2$ | 800 g/m$^2$ |
| Diisopropanolamine/S-Flurbiprofen (weight ratio) | 0.67 | 0.67 | 0.67 | 2.00 | 0.67 | 6.67 | amount (w/w %)

Test Example 5

The presence or absence of crystal precipitation of the drug in the pasty preparation of each formulation prepared above was observed by using a polarizing microscope. Also, a rubber roll was rolled over the pasty preparation of each formulation, and the adhesive property and the shape retaining property of the pasty preparation were observed. Further, the pH of the pasty preparation of each formulation was also measured.

The results are shown in Table 10.

As shown in Table 10, regarding the patches of Examples 14 to 17, crystal precipitation of the drug was not observed in the pasty preparation, and the adhesive property and the shape retaining property of the pasty preparation were also excellent. In the patch of Comparative Example 10, crystals of the drug precipitated in the pasty preparation. In the patch of Comparative Example 11, crystal precipitation of the drug was not observed in the pasty preparation, but the pasty preparation was poorly solidified, the adhesive property and the shape retaining property were poor, and the formulation could not be used as an aqueous patch.

The pH of the pasty preparation in each Example was within a range of 4 to 7, the pH of the pasty preparation in Comparative Example 10 was 3.6, and the pH of the pasty preparation in Comparative Example 11 was 7.8. The formulations of Examples wherein the pH was within a range of 4 to 7 showed excellent drug solubility, and excellent adhesive property and shape retaining property. On the other hand, the formulation of Comparative Example 10 showed poor drug solubility, and the formulation of Comparative Example 11 showed poor adhesive property and shape retaining property. It is believed that crystals of the drug precipitated in the pasty preparation in Comparative Example 10 because the pH of the pasty preparation was low, although the weight ratio of diisopropanolamine/S-flurbiprofen in the formulation of Comparative Example 10 was 0.67 like Examples 14 to 16. It is believed that the adhesive property and the shape retaining property in Comparative Example 11 could not be maintained because the pH of the pasty preparation was too high.

TABLE 10

| Pasty preparation | Ex. 14 | Ex. 15 | Ex. 16 | Ex. 17 | Com. 10 | Com. 11 |
|---|---|---|---|---|---|---|
| Crystal precipitation of the drug | No precipitate | No precipitate | No precipitate | No precipitate | Certain degree of precipitate | No precipitate |
| Adhesive property and shape retaining property | Excellent | Excellent | Excellent | Excellent | Excellent | Poorly solidified pasty preparation, and significantly poor adhesive property and shape retaining property |
| pH | 4.2 | 4.8 | 5.8 | 6.7 | 3.6 | 7.8 |

Example 18

An aqueous patch was prepared by using the ingredients described in Table 11 and the following procedures.

S-Flurbiprofen and diisopropanolamine were added to purified water and dissolved therein (Solution).

Sodium polyacrylate, sodium carboxymethyl cellulose, hydroxypropyl cellulose, and dihydroxyaluminum aminoacetate were added to concentrated glycerin and dispersed therein (Dispersion).

Purified water, a solution obtained by dissolving polyvinyl alcohol in purified water, a solution obtained by dissolving polyacrylic acid in purified water, sorbitol solution (70% D-sorbitol), kaolin, tartaric acid, sodium edetate, and crotamiton were mixed, and the resulting liquid was stirred and gradually mixed with the Dispersion. Then, the Solution was added thereto, and the resulting mixture was stirred to prepare a pasty preparation.

The pasty preparation was spread between a polyester non-woven fabric and a polyester film and cut into an appropriate size to prepare an aqueous patch.

Examples 19, 20, 21, 22, and 23

Desired aqueous patches were prepared by using ingredients described in Table 11 according to the procedures described in Example 18.

TABLE 11

| Ingredients | Ex. 18 | Ex. 19 | Ex. 20 | Ex. 21 | Ex. 22 | Ex. 23 |
| --- | --- | --- | --- | --- | --- | --- |
| S-Flurbiprofen | 0.5 | 1.5 | 1.5 | 1.5 | 1.5 | 2.5 |
| Diisopropanolamine | 1 | 1 | 1 | 1 | 1 | 1 |
| Concentrated glycerin | 17 | 17 | 17 | 17 | 17 | 17 |
| Sorbitol solution | 25 | 25 | 25 | 25 | 25 | 25 |
| Polyvinyl alcohol | 0.25 | 0.25 | 0.25 | 0.25 | 0.25 | 0.25 |
| Polyacrylic acid | 4 | 4 | 4 | 4 | 4 | 4 |
| Sodium polyacrylate | 5 | 5 | 5 | 5 | 5 | 5 |
| Sodium carboxymethyl cellulose | 4 | 4 | 4 | 4 | 4 | 4 |
| Hydroxypropyl cellulose | 0.25 | 0.25 | 0.25 | 0.25 | 0.25 | 0.25 |
| Dihydroxyaluminum aminoacetate | 0.06 | 0.06 | 0.06 | 0.06 | 0.06 | 0.06 |
| Kaolin | 1 | 1 | 1 | 1 | 1 | 1 |
| Tartaric acid | 1 | 1 | 1 | 1 | 1 | 1 |
| Sodium edetate | 0.06 | 0.06 | 0.06 | 0.06 | 0.06 | 0.06 |
| Crotamiton | 0.37 | | 0.18 | 0.37 | 0.75 | 0.37 |
| Purified water | 40.51 | 39.88 | 39.70 | 39.51 | 39.13 | 38.51 |
| Pasty preparation weight | 800 g/m$^2$ | 800 g/m$^2$ | 800 g/m$^2$ | 800 g/m$^2$ | 800 g/m$^2$ | 800 g/m$^2$ |
| Diisopropanolamine/S-Flurbiprofen (weight ratio) | 2.00 | 0.67 | 0.67 | 0.67 | 0.67 | 0.40 | amount (w/w %)

Test Example 6

Each test formulation was wrapped in an aluminum laminate film, and the outer periphery of the film was heat sealed to seal the formulation. The sealed products were stored in a thermostat bath at the temperature of 4° C., 25° C., or 40° C., taken out with time, and the presence or absence of crystal precipitation of the drug in the pasty preparation was observed by a polarizing microscope.

The observed results are shown in Table 12.

As shown in Table 12, regarding the patches of Examples 18 to 23, crystal precipitation of the drug was not observed and the dissolved state was maintained even after 6-months storage at 25° C. or 40° C. Further, regarding the formulations of Examples 18 and 20 to 23 comprising crotamiton, a crystal of the drug did not precipitate even under the storage conditions at 4° C. Accordingly, it was proved that the aqueous patch of the present invention was a formulation showing high drug stability. Further, it was proved that the aqueous patch of the present invention comprising crotamiton was a formulation having very high stability which can maintain the drug-dissolved state over a long period of time even under a severely low temperature storage condition.

TABLE 12

| Test formulation | Storage period | | 1 month | | | 2 months | | | 3 months | | | 6 months | | |
| --- | --- | --- | --- | --- | --- | --- | --- | --- | --- | --- | --- | --- | --- | --- |
| | S-Flurbiprofen | Crotamiton | 4° C. | 25° C. | 40° C. | 4° C. | 25° C. | 40° C. | 4° C. | 25° C. | 40° C. | 4° C. | 25° C. | 40° C. |
| Ex. 18 | 0.5% | 0.37% | − | − | − | − | − | − | − | − | − | − | − | − |
| Ex. 19 | 1.5% | 0% | − | − | − | − | − | − | + | − | − | + | − | − |
| Ex. 20 | | 0.18% | − | − | − | − | − | − | − | − | − | − | − | − |
| Ex. 21 | | 0.37% | − | − | − | − | − | − | − | − | − | − | − | − |

TABLE 12-continued

| Test formulation | Storage period | | 1 month | | | 2 months | | | 3 months | | | 6 months | | |
|---|---|---|---|---|---|---|---|---|---|---|---|---|---|---|
| | S-Flurbiprofen | Crotamiton | 4° C. | 25° C. | 40° C. | 4° C. | 25° C. | 40° C. | 4° C. | 25° C. | 40° C. | 4° C. | 25° C. | 40° C. |
| Ex. 22 | | 0.75% | – | – | – | – | – | – | – | – | – | – | – | – |
| Ex. 23 | 2.5% | 0.37% | – | – | – | – | – | – | – | – | – | – | – | – |

– No precipitate
+ Small amount of crystal precipitate of the drug
++ Large amount of crystal precipitate of the drug Example 24

An aqueous patch was prepared by using the ingredients described in Table 13 and the following procedures.

S-Flurbiprofen and diisopropanolamine were added to purified water and dissovled therein (Solution).

Polyacrylic acid, sodium polyacrylate, sodium carboxymethyl cellulose, and synthetic hydrotalcite were added to concentrated glycerin and dispersed therein (Dispersion).

Purified water, sorbitol solution (70% D-sorbitol), kaolin, tartaric acid, and crotamiton were mixed, and the resulting liquid was stirred and gradually mixed with the Dispersion. Then, the Solution was added thereto, and the resulting mixture was stirred to prepare a pasty preparation.

The pasty preparation was spread between a polyester non-woven fabric and a polyester film and cut into an appropriate size to prepare an aqueous patch.

Comparative Examples 12 and 13

The patch of Comparative Example 12 was prepared by reproducing the "Present invention product 12" described in Example 6 of the Patent Document 1. Also, the patch of Comparative Example 13 was prepared on the basis of the patch of Comparative Example 12 by increasing the concentration of S-flurbiprofen from 0.3% to 1.5%, and decreasing the concentration of purified water from 49.05% to 47.85%.

Comparative Examples 14 and 15

The patch of Comparative Example 14 was prepared by reproducing the Poultice cataplasm A in Examples of the Patent Document 2. The patch of Comparative Example 15 was prepared on the basis of the patch of Comparative Example 14 by increasing the concentration of S-flurbiprofen from 0.2% to 1.5%, and decreasing the concentration of purified water from 49.2% to 47.9%.

TABLE 13

| Ingredients | Ex. 24 | Com. 12 | Com. 13 | Com. 14 | Com. 15 |
|---|---|---|---|---|---|
| S-Flurbiprofen | 1.5 | 0.3 | 1.5 | 0.2 | 1.5 |
| Diisopropanolamine | 1 | | | | |
| Concentrated glycerin | 17 | 15 | 15 | 25 | 25 |
| Sorbitol solution | 17.5 | 10 | 10 | | |
| Propylene glycol | | 5 | 5 | | |
| Polyacrylic acid | 4 | 4.5 | 4.5 | | |
| Sodium polyacrylate | 5 | 1.5 | 1.5 | 5 | 5 |
| Sodium carboxymethyl cellulose | 4 | 4 | 4 | 4 | 4 |
| Methyl acrylate•2-ethylhexyl acrylate copolymer resin emulsion | | | | 6 | 6 |
| Aluminum hydroxide | | 0.1 | 0.1 | | |
| Synthetic hydrotalcite | 0.07 | 0.05 | 0.05 | | |
| Kaolin | 1 | 6 | 6 | 10 | 10 |
| Titanium oxide | | 0.5 | 0.5 | | |
| Tartaric acid | 1.5 | | | | |
| L-Menthol | | 3 | 3 | | |
| Mentha oil | | | | 0.3 | 0.3 |
| Polyoxyethylene glycol ether | | 1 | 1 | | |
| Propylene glycol caprylate | | | | 0.3 | 0.3 |
| Crotamiton | 0.4 | | | | |
| Purified water | 47.03 | 49.05 | 47.85 | 49.2 | 47.9 |
| Pasty preparation weight | 800 g/m² | 800 g/m² | 800 g/m² | 1428 g/m² | 1428 g/m² |
| Diisopropanolamine/ S-Flurbiprofen (weight ratio) | 0.67 | — | — | — | — | amount (w/w %)

Test Example 7

The presence or absence of crystal precipitation of the drug in the pasty preparation of each formulation prepared above was observed by using a polarizing microscope. Also, a rubber roll was rolled over the pasty preparation of each formulation, and the adhesive property and the shape retaining property of the pasty preparation were observed. Further, the tack force of the pasty preparation of each formulation was measured on the basis of JISZ0237 tack test method (hereinafter referred to as "ball tack test"). The results are shown in Table 14.

As shown in Table 14, regarding the patch of Example 24, crystal precipitation of the drug was not observed in the pasty preparation, and the adhesive property and the shape retaining property were also excellent. Also, regarding the tack force of the pasty preparation, the pasty preparation retained a steel ball having a diameter of 23.8 mm, and had a preferred tack force for an aqueous patch.

Meanwhile, regarding the patch of Comparative Example 12, crystal precipitation of the drug was not observed in the pasty preparation, and the adhesive property and the shape retaining property of the pasty preparation were also excellent, but, in the ball tack test, the pasty preparation could retain only a relatively small steel ball having a diameter of 14.3 mm, and thus the adhesive force of the formulation was poor. Also, regarding the patch of Comparative Example 13, which had the same base ingredients as the patch of Comparative Example 12 and in which the concentration of the drug was increased to 1.5%, a large amount of crystals of the drug precipitated, and the adhesive property and the shape retaining property were also poor. Also, in the ball tack test, the pasty preparation could retain a steel ball having a diameter of 9.5 mm at most, and the adhesive force of the formulation was very poor.

Further, regarding the patch of Comparative Example 14, crystal precipitation of the drug was not observed in the pasty preparation, but the pasty preparation was not solidified, and the adhesive property and the shape retaining property were significantly poor. Similarly, regarding the patch of Comparative Example 15, which had the same base ingredients as the patch of Comparative Example 14 and in which the concentration of the drug was increased to 1.5%, the pasty preparation was not solidified, a large amount of crystals of the drug precipitated, and the adhesive property and the shape retaining property of the formulation were significantly poor. The patches of Comparative Examples 14 and 15 could not retain any steel ball, and were proved to be formulations having very poor tack force.

TABLE 14

| Pasty preparation | Example 24 | Comparative Example 12 | Comparative Example 13 | Comparative Example 14 | Comparative Example 15 |
|---|---|---|---|---|---|
| Crystal precipitation of the drug | No precipitate | No precipitate | Large amount of drug precipitate | No precipitate | Large amount of drug precipitate |
| Adhesive property and shape retaining property | Excellent | Excellent | Excellent shape retaining property, but poor adhesive property | Unsolidified pasty preparation, and significantly poor adhesive property and shape retaining property | Unsolidified pasty preparation, and significantly poor adhesive property and shape retaining property |
| Ball tack test | Diameter 23.8 mm | Diameter 14.3 mm | Diameter 9.5 mm | Unmeasurable | Unmeasurable |

Test Example 8

Each patch of Example 24 and Comparative Examples 12, 13, 14, and 15 was subjected to an in vitro transdermal permeation test of the drug using an excised abdominal skin of a hairless rat. The test method is shown as follows, and the test results are shown in FIG. 1.

(Test method)

An abdominal skin of a hairless rat was excised, and put on a Franz diffusion cell. The dermis side was set to be the receptor side, phosphate buffer solution was injected inside of the receptor side, the temperature was kept at 37° C., and the solution was stirred. Each test formulation was cut into a round shape having a diameter of 14 mm, applied to the skin, the receptor solution was sampled, and the amount of the drug in each test formulation permeated the skin and moved to the buffer solution (permeation amount) was measured by using a liquid chromatography equipment.

The test results were evaluated by the cumulative permeation amount of the drug after 24 hours from the start of the test ($\mu g/cm^2 \cdot 24$ hr).

According to the results shown in FIG. 1, the patch of Example 24 showed the highest permeation amount, and is believed to be a formulation achieving excellent therapeutic effects.

Meanwhile, the permeation amounts in the patches of Comparative Examples 12 and 14 were very low. Regarding the patches of Comparative Examples 13 and 15, which have the same base ingredients as the patches of Comparative Examples 12 and 14 respectively and in which only the amounts of the drug were increased, the permeation amounts were slightly increased, but were lower as compared to the patch of Example 24 comprising the same amount of the drug. It is believed that said results were caused by the crystal precipitation of the drug in the pasty preparation of Comparative Example 13 or Comparative Example 15.

Test Example 9

The patch of Example 24, the patch of Example 25 which comprises the same base ingredients as the patch of Example 24 and R-flurbiprofen instead of S-flurbiprofen, and a commercially available tape formulation (comprising 2.38% of racemic flurbiprofen) were used as test formulations to carry out anti-inflammatory tests using a rat, and the effects were compared with each other. The test method is described below, and the test results are shown in Table 15.

(Test Method)

A paw volume of a rat was measured (initial volume), and then each test formulation (3×4 cm) was applied and fixed on the paw. After 4 hours from the application, each test formulation was removed, and 1% carrageenin suspension (0.1 mL) was injected into the paw to initiate paw edema. After 2, 3, and 4 hours from the initiation, the paw volume was measured, and the edema rate ((Paw volume after carrageenin injection−initial volume)/initial volume×100) of each animal was calculated.

The patches of Examples 24 and 25 were found to suppress edema and have anti-inflammatory actions. Especially, the effect of the patch of Example 24 comprising S-flurbiprofen was prominent, and more excellent than that achieved by the commercially available tape formulation.

TABLE 15

| Test | After initiation | | |
|---|---|---|---|
| formulation | 2 hr | 3 hr | 4 hr |
| Untreated | 71.1 | 76.1 | 71.0 |
| Example 24 | 34.6 | 38.1 | 37.4 |
| Example 25 | 55.4 | 64.9 | 65.6 |
| Commercially available tape formulation | 44.1 | 47.7 | 46.7 | edema rate (%) (n = 8)

Example 26

An aqueous patch was prepared by using the ingredients described in Table 16 and the following procedures.

An active ingredient and diisopropanolamine were added to purified water and dissolved therein (Solution).

Concentrated glycerin, propylene glycol, sodium polyacrylate, sodium carboxymethyl cellulose, and magnesium aluminometasilicate were mixed and dispersed in the resulting liquid (Dispersion).

Purified water, a solution obtained by dissolving polyacrylic acid in purified water, a sorbitol solution (70% D-sorbitol), kaolin, and tartaric acid were mixed, and the resulting liquid was stirred and gradually mixed with the Dispersion. Then, the Solution was added thereto, and the resulting mixture was stirred to prepare a pasty preparation.

The pasty preparation was spread between a non-woven fabric and a polyester film and cut into an appropriate size to prepare an aqueous patch.

Example 27

A desired aqueous patch was prepared by using the ingredients described in Table 16 according to the procedures described in Example 26.

Comparative Examples 16 and 17

Desired aqueous patches were prepared by using the ingredients described in Table 16 according to the procedures described in Example 26.

TABLE 16

| Ingredients | Ex. 26 | Ex. 27 | Com. 16 | Com. 17 |
|---|---|---|---|---|
| S-Ketoprofen | 1.5 | | 0.75 | |
| S-Ibuprofen | | 1.5 | | 0.75 |
| R-Ketoprofen | | | 0.75 | |
| R-Ibuprofen | | | | 0.75 |
| Diisopropanolamine | 1 | 1 | 1 | 1 |
| Propylene glycol | 5 | 5 | 5 | 5 |
| Concentrated glycerin | 20 | 20 | 20 | 20 |

TABLE 16-continued

| Ingredients | Ex. 26 | Ex. 27 | Com. 16 | Com. 17 |
|---|---|---|---|---|
| Sodium polyacrylate | 5 | 5 | 5 | 5 |
| Sodium carboxymethyl cellulose | 4.5 | 4.5 | 4.5 | 4.5 |
| Sorbitol solution | 20 | 20 | 20 | 20 |
| Kaolin | 1 | 1 | 1 | 1 |
| Polyacrylic acid | 1 | 1 | 1 | 1 |
| Magnesium aluminometasilicate | 0.1 | 0.1 | 0.1 | 0.1 |
| Tartaric acid | 0.5 | 0.5 | 0.5 | 0.5 |
| Purified water | 40.40 | 40.40 | 40.40 | 40.40 |
| Pasty preparation weight | 500 g/m$^2$ | 500 g/m$^2$ | 500 g/m$^2$ | 500 g/m$^2$ |
| Diisopropanolamine/Drug (weight ratio) | 0.67 | 0.67 | 0.67 | 0.67 | amount (w/w %)

Test Example 10

The drug condition in the pasty preparation of each formulation prepared above was observed by using a polarizing microscope.

The results are shown in Table 17.

As shown in Table 17, while precipitation of the drug in the pasty preparation was not observed in the patches of Example 26 and Example 27, a large amount of the drug precipitated in the patches of Comparative Example 16 and Comparative Example 17 comprising enantiomers at the ratio of 1:1 (racemate).

While the formulations comprising only one of the enantiomers of the drug could dissolve the drug well like the formulation comprising flurbiprofen, the formulations comprising a mixture of enantiomers significantly deteriorated the solubility.

TABLE 17

| Pasty preparation | Ex. 26 | Ex. 27 | Com. 16 | Com. 17 |
|---|---|---|---|---|
| Drug condition | No precipitate | No precipitate | Large amount of precipitate | Large amount of precipitate |

INDUSTRIAL APPLICABILITY

According to the present invention, an aqueous patch which can stably comprise only one of an S-enantiomer and an R-enantiomer of a drug capable of being present in such enantiomers at a relatively high concentration over a long period of time, has the excellent adhesive property and the excellent shape retaining property, and achieves high skin permeability of the drug, can be provided. The aqueous patch of the present invention is useful as, for example, an aqueous patch having anti-inflammatory actions.

The invention claimed is:

1. An aqueous patch comprising only one of enantiomers of a drug as an active ingredient in a pasty preparation comprising a water-soluble organic amine,
   wherein an amount of the water-soluble organic amine is 0.2 to 5 w/w% relative to a total weight of the pasty preparation,
   wherein a weight ratio of the water-soluble organic amine relative to the enantiomer of the drug is 0.25 to 5,
   wherein the drug is one or more selected from the group consisting of flurbiprofen, ketoprofen, and ibuprofen, and wherein the water-soluble organic amine is one or more selected from the group consisting of diisopropanolamine, monoethanolamine, diethanolamine, triethanolamine, and triethylamine.

2. The aqueous patch according to claim 1, wherein the drug is flurbiprofen.

3. The aqueous patch according to claim 1, wherein an amount of the drug is 0.5 to 6 w/w % relative to a total weight of the pasty preparation.

4. The aqueous patch according to claim 1, wherein the enantiomer of the drug is an S-enantiomer.

5. The aqueous patch according to claim 1, which further comprises one or more ingredient(s) selected from the group consisting of water, polyacrylic acid or a salt thereof, a cellulose derivative, a cross-linking agent, a humectant, and a pH regulator in the pasty preparation.

6. The aqueous patch according to claim 5, wherein
the polyacrylic acid or a salt thereof is one or more selected from the group consisting of polyacrylic acid, sodium polyacrylate, and partially neutralized polyacrylate;
the cellulose derivative is one or more selected from the group consisting of sodium carboxymethyl cellulose, hydroxypropyl cellulose, and hydroxymethyl cellulose;
the cross-linking agent is one or more selected from the group consisting of dihydroxyaluminum aminoacetate, magnesium aluminometasilicate, aluminum hydroxide, and synthetic hydrotalcite;
the humectant is one or more selected from the group consisting of glycerin, 1,3-butylene glycol, propylene glycol, polypropylene glycol, D-sorbitol, and polyethylene glycol 400; and
the pH regulator is one or more selected from the group consisting of tartaric acid, lactic acid, and malic acid.

7. The aqueous patch according to claim 5, wherein an amount of the water is 20 to 70 w/w %, an amount of the polyacrylic acid or a salt thereof is 2 to 20 w/w %, an amount of the cellulose derivative is 2 to 20 w/w %, an amount of the cross-linking agent is 0.02 to 3.5 w/w %, an amount of the humectant is 5 to 60 w/w %, and an amount of the pH regulator is 0.2 to 10 w/w %, relative to a total weight of the pasty preparation.

* * * * *